(12) United States Patent
Kim (10) Patent No.: US 9,923,030 B2
(45) Date of Patent: Mar. 20, 2018

(54) ORGANIC LIGHT-EMITTING DEVICE

(71) Applicant: LG Display Co., Ltd., Seoul (KR)

(72) Inventor: Kwanghyun Kim, Daegu (KR)

(73) Assignee: LG Display Co., Ltd., Seoul (KR)

( * ) Notice: Subject to any disclaimer, the term of this patent is extended or adjusted under 35 U.S.C. 154(b) by 149 days.

(21) Appl. No.: 14/948,579

(22) Filed: Nov. 23, 2015

(65) Prior Publication Data

US 2016/0155977 A1   Jun. 2, 2016

(30) Foreign Application Priority Data

Nov. 27, 2014   (KR) .................. 10-2014-0167446

(51) Int. Cl.
| | | |
|---|---|---|
| H01L 51/00 | (2006.01) | |
| H01L 27/32 | (2006.01) | |
| H01L 51/50 | (2006.01) | |
| C07F 15/00 | (2006.01) | |
| C09K 11/06 | (2006.01) | |
| C07F 5/06 | (2006.01) | |
| C07F 3/00 | (2006.01) | |

(52) U.S. Cl.
CPC .......... *H01L 27/3206* (2013.01); *C07F 3/006* (2013.01); *C07F 5/06* (2013.01); *C07F 15/0033* (2013.01); *C09K 11/06* (2013.01); *H01L 51/5016* (2013.01); *H01L 51/0072* (2013.01); *H01L 51/0081* (2013.01); *H01L 51/0085* (2013.01); *H01L 51/0094* (2013.01); *H01L 2251/5384* (2013.01); *H01L 2251/552* (2013.01)

(58) Field of Classification Search
CPC ............ H01L 51/0072; H01L 51/5012; H01L 51/0081; H01L 51/0085; H01L 51/0094; H01L 51/5016; H01L 2251/5384; H01L 2251/552; C09K 11/06; C07F 15/0033; C07F 3/006; C07F 5/06
USPC ............ 257/40, E51.022; 428/690; 252/500, 252/301.16; 438/35, 34
See application file for complete search history.

(56) References Cited

U.S. PATENT DOCUMENTS

| | | | | |
|---|---|---|---|---|
| 2009/0045736 A1* | 2/2009 | Kho | ..................... | H01L 51/5036 313/504 |
| 2011/0240965 A1* | 10/2011 | Yoon | ..................... | H01L 27/3211 257/40 |
| 2015/0060801 A1* | 3/2015 | Nishimura | .......... | H01L 51/0067 257/40 |
| 2015/0187848 A1* | 7/2015 | Kim | ..................... | H01L 27/3211 257/40 |
| 2016/0141521 A1* | 5/2016 | Watanabe | .............. | C09K 11/06 257/40 |
| 2016/0155977 A1* | 6/2016 | Kim | ..................... | H01L 51/5016 257/40 |

\* cited by examiner

*Primary Examiner* — Amanda C Walke
(74) *Attorney, Agent, or Firm* — Morgan, Lewis & Bockius LLP (57) ABSTRACT

An organic light-emitting device includes a red emission layer formed by mixing a first host made of a carbazole-based material, a second host made of a metal complex and a dopant. Accordingly, the driving voltage of the organic light-emitting device can be reduced, and thus power consumption of the organic light-emitting device can be improved. In addition, by mixing the first host and the second host having differences in energy level in the red emission layer, the luminous efficiency of the red emission layer of the organic light-emitting device can be improved. Thus, the lifetime of the organic light-emitting device can be elongated.

16 Claims, 4 Drawing Sheets

|  | VOLTAGE (V) | | EFFICIENCY (cd/A) | LIFETIME (hrs@T$_{95}$) |
| --- | --- | --- | --- | --- |
|  | TURN-ON VOLTAGE | DRIVING VOLTAGE | | |
| COMPARATIVE EXAMPLE 1 | 2.2 | 4.9 | 55 | 550 |
| COMPARATIVE EXAMPLE 2 | 2.6 | 5.1 | 48 | 100 |
| EMBODIMENT | 2.4 | 4.6 | 65 | 820 |

ORGANIC LIGHT-EMITTING DEVICE

CROSS-REFERENCE TO RELATED APPLICATIONS

This application claims the priority of Korean Patent Application No. 10-2014-0167446 filed on Nov. 27, 2014, in the Korean Intellectual Property Office, the disclosure of which is incorporated herein by reference.

BACKGROUND

Technical Field

The present disclosure relates to an organic light-emitting device, and more particularly, to an organic light-emitting device that is driven with low voltage and has improved efficiency and lifetime.

Description of the Related Art

An organic light-emitting device (OLED) display is a self-luminous display. In such an OLED display, electrons and holes are injected into an emission layer from a cathode and an anode, respectively, and they are combined to form excitons. Light is emitted when the excitons drop from the excited state to the ground state.

OLED displays can be sorted into a top emission OLED display, a bottom emission OLED display and a dual emission OLED display depending on the direction light is emitted. Further, OLED displays can be sorted into a passive matrix OLED display and an active matrix OLED display depending on the driving manner.

An OLED display does not require an additional light source, unlike liquid crystal diode (LCD) displays. Therefore, OLED displays can be made lighter and thinner than LCD displays. Further, an OLED display has advantages in that it is driven with low voltage to consume less power, and that it can represent more vivid colors. Further, it has short response time, wide viewing angle and good contrast ratio (CR). For these reasons, an OLED display is currently under development as the next generation display device.

As high-definition displays become more prominent, the number of pixels per unit area increases, and high luminance is required. However, the luminance (Cd) per unit area (A) is limited by the structure of related art OLED displays. In addition, as the amount of applied current increases, reliability of an OLED display is degraded, and power consumption increases.

Accordingly, in order to improve quality and productivity of OLED displays, it is necessary to increase the luminous efficiency and lifetime of the OLED displays and reduce power consumption. There are a variety of on-going research activities regarding organic light-emitting devices capable of improving luminous efficiency, lifetime and viewing angle while maintaining the area for reproducing colors.

Typically, an OLED emits light in such a manner that (a) holes injected from a first electrode i.e., an anode to transfer through a hole injection layer (HIL) and a hole transporting layer (HTL) and (b) electrons injected from a second electrode i.e., a cathode to transfer through an electron injection layer (EIL) and an electron transporting layer (ETL) recombine in an emission layer (EML).

For an organic light-emitting device to increase the luminous efficiency of the emission layer, it is required to increase the concentrations of holes and electrons injected into the emission layer, and form the holes and electrons with materials of high concentration.

In addition, light is not generated in the entire region of the organic light-emitting device. Rather, it is only generated at positions where holes and electrons meet and recombine. Thus, the characteristics of the organic light-emitting device can be improved by taking into account the area where recombination occurs.

For a top-emission organic light-emitting device, there is a general trend toward employing red phosphorescent host material as a red emission layer, which has higher luminous efficiency than existing red fluorescent host material, in order to increase the red luminous efficiency among red, green and blue sub-pixels.

Typically, an organic light-emitting device is produced by thermal evaporation, in which a fine metal mask is used to selectively form an organic layer, so that functional layers and an emission layer required by the organic light-emitting device are formed.

For an organic light-emitting device produced using such a fine metal mask, a red emission layer made of a single red phosphorescent host material has an advantage in that it exhibits high efficiency. However, it has a shorter lifetime than an organic light-emitting device including a red emission layer made of an existing red fluorescent host material, which is still a challenge to be overcome.

Further, for an organic light-emitting device including a red emission layer made of a single red phosphorescent host material, it is required to improve power consumption by increasing efficiency and reducing driving voltage.

In view of the above, the present disclosure addresses these issues and provides an organic light-emitting device that is driven with low voltage and has improved efficiency and lifetime.

Aspects of the present disclosure are not limited to that described above and other aspects will be clearly understood by those skilled in the art from the following description.

SUMMARY

Accordingly, the present invention is directed to an organic light-emitting device that substantially obviates on ore more of the problems due to limitations and disadvantages of the related art.

An object of the present invention is to provide an organic light-emitting device that is driven with low voltage and has improved efficiency and lifespan.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, an organic light-emitting device comprises a first electrode and a second electrode; and an emission layer disposed between the first electrode and the second electrode over a plurality of sub-pixel regions, the emission layer comprising a red emission layer, a green emission layer and a blue emission layer. The red emission layer includes a first host, a second host and a dopant, and the first host is made of a carbazole-based material, and the second host is made of a metal complex.

A LUMO energy level of the first host may be between 2.2 eV and 2.8 eV, and a HOMO energy level of the first host may be between 5.1 eV and 5.7 eV.

A LUMO energy level of the second host may be between 2.4 eV and 3.0 eV, and a HOMO energy level of the second host may be between 5.2 eV and 5.8 eV.

The difference between a LUMO energy level of the first host and a LUMO energy level of the second host may be equal to or larger than 0.2.

The difference between a HOMO energy level of the first host and a HOMO energy level of the second host may be equal to or larger than 0.1.

The mobility of each of the first host and the second host may be between $10^{-4}$ $cm^2/Vs$ and $10^{-6}$ $cm^2/Vs$.

The mixing ratio between the first host and the second host in the red emission layer may be between 1:3 and 3:1.

The first host may be made of one of CBP, CDBP and mCP.

The second host may be made of a beryllium-based complex or an aluminum-based complex.

The first host and the second host may be made of a phosphorescent material.

The thickness of the red emission layer may be between 300 Å and 500 Å.

The dopant may be made of a phosphorescent material.

The doping concentration of the dopant may be between 1% and 10%.

In another aspect, an organic light-emitting device comprises a red emission layer comprising a first host having a lowest unoccupied molecular orbital (LUMO) energy level and a highest unoccupied molecular orbital (HOMO) energy level and a second host having a LUMO energy level and a HOMO energy level that are different from those of the first host, resulting in an area for recombination of electrons and holes being formed within the red emission layer. The area for recombination being expanded compared to a related art red emission layer having only a single host resulting in an area for recombination being formed only at an interface between a hole transporting layer and the red emission layer.

The red emission layer may be implemented in an organic light-emitting display device.

According to the present disclosure, an organic light-emitting device includes a red emission layer formed by mixing a first host made of a carbazole-based material, a second host made of a metal complex and a dopant. Accordingly, the driving voltage of the organic light-emitting device can be reduced, and thus power consumption of the organic light-emitting device can be improved.

In addition, by mixing the first host and the second host having differences in energy level in the red emission layer, the luminous efficiency of the red emission layer of the organic light-emitting device can be improved. Thus, the lifetime of the organic light-emitting device can be elongated.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in anc constitute a part of this specification illustrate embodiments of the invention and together with the description serve to explain the principles of the invention. In the drawings.

DETAILED DESCRIPTION OF THE ILLUSTRATED EMBODIMENTS

The figures, dimensions, ratios, angles, numbers of elements given in the drawings are merely illustrative and are not limiting. Like reference numerals denote like elements throughout the description. Further, in describing the present disclosure, descriptions on well-known technologies may be omitted in order not to obscure the gist of the present disclosure. It is to be noticed that the terms "comprising," "having," "including" and so on, used in the description and claims, should not be interpreted as being restricted to the means listed thereafter unless specifically stated otherwise. Where an indefinite or definite article is used when referring to a singular noun, e.g. "a," "an," "the," this includes a plural of that noun unless specifically stated otherwise.

In describing elements, they are interpreted as including error margins even without explicit statements. In describing positional relationships, such as "an element A on an element B," "an element A above an element B," "an element A below an element B" and "an element A next to an element B," another element C may be disposed between the elements A and B unless the term "directly" or "immediately" is explicitly stated.

Although the terms such as first, second, etc. are used to provide distinction between the elements, these terms are not necessarily intended to indicate temporal or other prioritization of such elements. Theses terms are used to merely distinguish one element from another. Accordingly, as used herein, a first element may be a second element within the technical aspects of the present disclosure.

Features of various embodiments of the present disclosure may be combined partially or totally. As will be clearly appreciated by those skilled in the art, technically various interactions and operations are possible. Various embodiments can be practiced individually or in combination.

Hereinafter, embodiments of the present disclosure will be described in detail with reference to the accompanying drawings.

Figure 1:
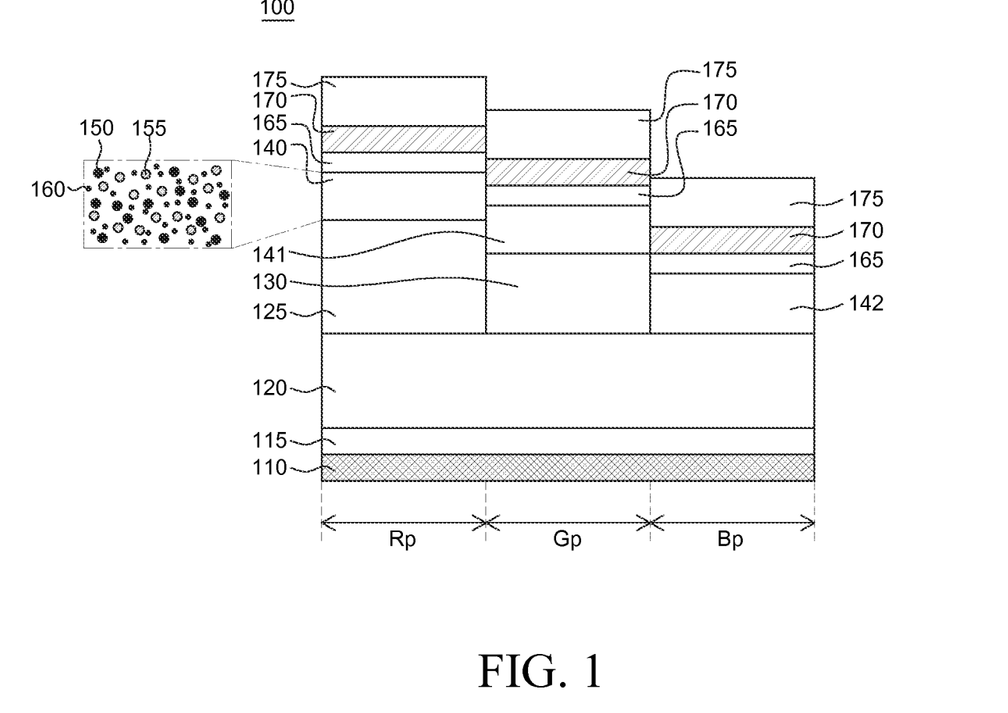
FIG. 1 is a cross-sectional view showing an organic light-emitting device according to an example embodiment of the present disclosure.

FIG. 1 is a cross-sectional view showing an organic light-emitting device according to an example embodiment of the present disclosure.

As shown in FIG. 1, an organic light-emitting device 100 may include: a first electrode (anode) 110 formed on a substrate where a red sub-pixel region Rp, a green sub-pixel region Gp and a blue sub-pixel region Bp are defined; a hole injection layer (HIL) 115; a hole transporting layer (HTL) 120; a R-hole transporting layer (R-HTL) 125; and a G-hole transporting layer (G-HTL) 130.

Further, the organic light-emitting device 100 may include: an emission layer (EML) including a red emission layer (Red EML) 140 formed in the red sub-pixel region Rp, a green emission layer (Green EML) 141 formed in the green sub-pixel region Gp and a blue emission layer (Blue EML) 142 formed in the blue sub-pixel region Bp; an electron transporting layer (ETL) 165; a second electrode (cathode) 170; and a capping layer (CPL) 175.

In an OLED display including organic light-emitting devices, gate lines and data lines are disposed on the substrate such that they intersect one another to define pixel regions (although pixel regions can also be defines by other structures), and a power line is disposed in parallel with the gate lines or the data lines. In each of the pixel regions, a switching thin-film transistor connected to a gate line and a data line, and a driving thin-film transistor connected to the switching thin-film transistor are disposed. The driving thin-film transistor is connected to the first electrode 110.

The first electrode 110 may be located on the substrate such that it corresponds to each of the red sub-pixel region Rp, the green sub-pixel region Gp, and the blue sub-pixel region Bp. The first electrode 110 may be a reflective electrode.

For example, the first electrode 110 may include a transparent conductive layer having a high work function such as indium-tin-oxide (ITO), and a reflective layer made of silver (Ag) or a silver alloy (Ag alloy).

The hole injection layer (HIL) 115 is disposed on the first electrode 110 such that it covers all of the red sub-pixel region Rp, the green sub-pixel region Gp, and the blue sub-pixel region Bp.

The hole injection layer 115 may serve to facilitate hole injection and may be made of, but is not limited to, at least one selected among a group consisting of HATCN, CuPc (cupper phthalocyanine), PEDOT (poly(3,4)-ethylenedioxy-thiophene), PANI (polyaniline) and NPD (N,N-dinaphthyl-N,N'-diphenylbenzidine).

The hole injection layer 115 may be formed by adding a p-dopant to the material of the hole transporting layer 120. In doing so, the hole injection layer 115 and the hole transporting layer 120 may be formed by the same processing equipment in a continuous process.

The hole transporting layer (HTL) 120 is disposed on the hole injection layer 115 as a common hole transporting layer (HTL) for the red sub-pixel region Rp, the green sub-pixel region Gp, and the blue sub-pixel region Bp.

The hole transporting layer 120 may serve to facilitate hole transportation and may be made of, but is not limited to, at least one selected among a group consisting of NPD (N,N-dinaphthyl-N,N'-diphenylbenzidine), TPD (N,N'-bis-(3-methylphenyl)-N,N'-bis-(phenyl)-benzidine), s-TAD and MTDATA (4,4',4"-Tris(N-3-methylphenyl-N-phenyl-amino)-triphenylamine).

The R-hole transporting layer 125 and the G-hole transporting layer 130 are disposed on the hole transporting layer 120. The R-hole transporting layer 125 is disposed in the red sub-pixel region Rp, and the G-hole transporting layer 130 is disposed in the green sub-pixel region Gp.

The R-hole transporting layer 125 works as a first hole transporting layer (R-hole transporting layer: R-HTL) formed in the red sub-pixel region Rp and may form an optical distance of a microcavity.

The R-hole transporting layer 130 works as a second hole transporting layer (G-hole transporting layer: G-HTL) formed in the green sub-pixel region Gp and may form an optical distance of a microcavity.

The R-hole transporting layer 125 and the G-hole transporting layer 130 may serve to facilitate hole transportation and may be made of, but is not limited to, at least one selected among a group consisting of NPD (N,N-dinaphthyl-N,N'-diphenylbenzidine), TPD (N,N'-bis-(3-methylphenyl)-N,N'-bis-(phenyl)-benzidine), s-TAD, and MTDATA (4,4',4"-Tris(N-3-methylphenyl-N-phenyl-amino)-triphenylamine).

Further, an electron blocking layer (EBL) may be formed on the R-hole transporting layer 125 and the G-hole transporting layer 130. The electron blocking layer (EBL) blocks electrons from going over to the hole transporting layer 120, so that recombination of holes and electrons in the emission layer is facilitated, thereby improving luminous efficiency of the organic light-emitting device.

The red emission layer (Red EML) 140 is disposed on the R-hole transporting layer 125 in the red sub-pixel region Rp. The red emission layer 140 may include a luminous material emitting red light. The luminous material may be formed using a phosphorescent material or a fluorescent material.

Referring to FIG. 1, in the organic light-emitting device 100, the red emission layer 140 includes a first host 150, a second host 155 and a dopant 160, unlike the related art red emission layer including only a single host and a dopant. In addition, in the organic light-emitting device 100, the first host 150, the second host 155 and the dopant 160 may be made of a phosphorescent material.

Further, in the organic light-emitting device 100, the first host 150 in the red emission layer 140 may be made of a carbazole-based material and the second host 155 in the red emission layer 140 may be made of a metal complex.

More specifically, the first host 150 included in the red emission layer 140 in the organic light-emitting device 100 may be made of a carbazole-based material. For example, the first host 150 may be made of, but is not limited to, one among 1) carbazole-based material, 2) CBP (4,4'-bis(carbazol-9-yl)biphenyl), 3) CDBP (4,4'-bis(carbazol-9-yl)-2,2'-dimethylbiphenyl), and 4) mCP (1,3-bis(carbazol-9-yl)benzene) expressed by the following structural formulas:

1)

2)

3)

4)

Further, the second host 155 included in the red emission layer 140 in the organic light-emitting device 100 may be made of a metal complex such as a beryllium-based complex or aluminum-based complex. For example, the second host 155 may be made of, but is not limited to, 1) $BeB_{q2}$ or 2) BAlq expressed by the following structural formulas:

1)

2)

Additionally, the first host 150 included in the red emission layer 140 of the organic light-emitting device 100 may be made of a material other than a carbazole-based material. For example, the first host 150 may be made of, but is not limited to, one among 1) TAZ (3-(4-biphenyl)-4-phenyl-5-(4-tert-butylphenyl)-1,2,4-triazole), 2) UGH1 (Bis(2-methylphenyl)diphenylsilane), 3) UGH2 (1,4-bis(triphenylsilyl)benzene), 4) UGH3 (1,3-bis(triphenylsilyl)benzene), 5) UGH4 (p-bis(triphenylsilyl)benzene), and 6) BCP (2,9-dimethyl-4,7diphenyl-1,10-phenanthroline) expressed by the following structural formulas:

1)

2)

UGH1

3)

UGH2

4)

UGH3

5)

UGH4

6)

In light of the process of forming the red emission layer 140, the mixing ratio between the first host 150 and the second host 155 in the red emission layer 140 may be between 1:3 and 3:1. Such range is set so as to avoid or minimize non-uniform deposition of the red emission layer 140 possibly occurring if either the first host 150 or the second host 155 is contained in a much greater amount than the other in a single deposition source.

The thickness of the red emission layer 140 can be determined by taking into account the optical distance of the organic light-emitting device 100. The thickness of the red emission layer 140 can be between 300 Å and 500 Å, since the thicker the red emission layer 140 is, the higher the driving voltage is.

Further, the dopant doped into the red emission layer 140 may be made of, but is not limited to, a phosphorescent material such as iridium complex including Ir(ppy)3 or Ir(mmapy)3.

The concentration of the dopant doped into the red emission layer 140 can be between 1% and 10%. If the concentration is too high, the dopant may work as a trap site in the red emission layer 140, which results in reduced luminous efficiency.

The green emission layer (Green EML) 141 is disposed on the G-hole transporting layer 130 in the green sub-pixel region Gp. The green emission layer 141 may include a luminous material emitting green light. The luminous material may be formed using a phosphorescent material or a fluorescent material.

The host material of the green emission layer 141 may be made of, but is not limited to, different kinds of phosphorescent materials selected among a group consisting of TCTA (Tris(4-carbazoyl-9-ylphenyl)amine), CBP (4,4'-Bis(N-carbazolyl)-1,1'-biphenyl), Balq (Bis(8-hydroxy-2-methylquinoline)-(4-phenylphenoxy)aluminum), and PPV (poly(p phenylene vinylene)).

The blue emission layer (Blue EML) 142 is disposed on a portion of the common hole transporting layer 120 in the blue sub-pixel region Bp, where neither the R-hole transporting layer 125 nor the G-hole transporting layer 130 is formed. The blue emission layer 142 may include a luminous material emitting blue color. The luminous material may be formed using a phosphorescent material or a fluorescent material.

The blue emission layer 142 may have a host material including CBP or mCP and may be made of a phosphorescent material containing a dopant material including (4,6-F2ppy)2Irpic. Alternatively, the blue emission layer 142 may be made of, but is not limited to, a fluorescent material including one selected among a group consisting of spiro-DPVBi, spiro-6P, distytylbenzene (DSB), distyrylarylene (DSA), a PFO-based polymer, and a PPV-based polymer.

The electron transporting layer (ETL) 165 is disposed on the red emission layer 140, the green emission layer 141 and the blue emission layer 142 such that it covers all of the red sub-pixel region Rp, the green sub-pixel region Gp, and the blue sub-pixel region Bp. The thickness of the electron transporting layer 165 may be adjusted depending on the electron transportation characteristics. In addition, the electron transporting layer 165 may be used for transporting and injecting electrons.

The electron transporting layer 165 may serve to facilitate electron transportation and may be made of, but is not limited to, at least one selected among a group consisting of Alq3 (tris(8-hydroxyquinolino)aluminum), PBD, TAZ, spiro-PBD, BAlq, Liquid (lithium quinolate), BMB-3T, PF-6P, TPBI, COT and SAlq.

An electron injection layer (EIL) may be additionally formed on the electron transporting layer 165.

The electron injection layer (EIL) may be, but is not limited to, Alq3 (tris(8-hydroxyquinolino)aluminum), PBD, TAZ, spiro-PBD, BAlq or SAlq.

It is to be understood that the structure of the organic light-emitting device 100 is not limited to that of the embodiment of the present disclosure. At least one of the hole injection layer 115, the hole transporting layer 120, the R-hole transporting layer 125, the G-hole transporting layer 130, the electron transporting layer 165 and the electron injection layer EIL may be eliminated. In addition, the hole injection layer 115, the hole transporting layer 120, the R-hole transporting layer 125, the G-hole transporting layer 130, the electron transporting layer 165 and the electron injection layer EIL may be structurally or functionally combined in a variety of ways or may be formed as two or more layers.

The second electrode 170 may be disposed on the electron transporting layer 165 such that it covers all of the red sub-pixel region Rp, the green sub-pixel region Gp, and the blue sub-pixel region Bp. For example, the second electrode 170 may be made of a material such as silver (Ag) or an alloy of silver (Ag) and magnesium (Mg), etc., and may be a transflective electrode. That is, some of the light generated in the emission layer exit through the transreflective second electrode 170, and other light reflected in the second electrode 170 may be reflected back to the first electrode 110.

As such, light is reflected between the first electrode 100 and the second electrode 170 working as reflective layers. By virtue of the microcavity effect due to such repeated reflection, light is reflected repeatedly between the first electrode 110 and the second electrode 170, such that the optical efficiency is increased.

It is also possible to form the first electrode 110 as a transparent electrode and the second electrode 170 as a reflective electrode, so that light generated in the emission layer exits through the first electrode 110.

A capping layer 175 is formed on the second electrode 170. The capping layer 175 functions to increase light extraction efficiency. The capping layer 175 may be made of one of host materials of the hole transporting 120, the R-hole transporting layer 125, the G-hole transporting layer 130, the electron transporting layer 165, the red emission layer 140, the green emission layer 141 and the blue emission layer 142. Alternatively, the capping layer 175 may be eliminated (not used).

Figure 2:
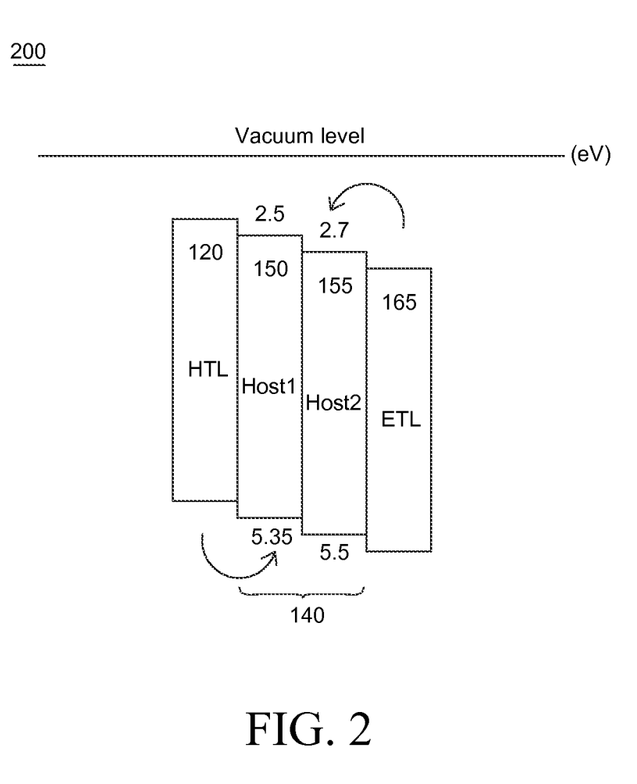
FIG. 2 is an energy band diagram of a first host and a second host included in a red emission layer, a hole transporting layer adjacent to the red emission layer, and an electron transporting layer of an organic light-emitting device according to an example embodiment of the present disclosure.

FIG. 2 is an energy band diagram of the red emission layer 140 including the first host 150 and the second host 155, the hole transporting layer 120 adjacent to the red emission layer 140, and the electron transporting layer 165 of the organic light-emitting device 100 according to the example embodiment of the present disclosure described with reference to FIG. 1.

More specifically, the organic light-emitting device 100 may includes the red emission layer 140 including the first host 150 and the second host 155, the hole transporting layer 120 disposed under the red emission layer 140, and the electron transporting layer 165 disposed on the red emission layer 140.

Referring to FIG. 2, the first host 150 included in the red emission layer 140 of the organic light-emitting device 100 may be a host capable of transporting holes. The lowest unoccupied molecular orbital (LUMO) energy level of the first host 150 may be between 2.2 eV and 2.8 eV, and 2.5 eV in this example embodiment.

The highest occupied molecular orbital (HOMO) energy level of the first host 150 may be between 5.1 eV and 5.7 eV, and 5.35 eV in this example embodiment.

The second host 155 included in the red emission layer 140 of the organic light-emitting device 100 may be a host capable of transporting electrons. The LUMO energy level of the second host 155 may be between 2.4 eV and 3.0 eV, and 2.7 eV in this example embodiment.

The HOMO energy level of the second host 155 may be between 5.2 eV and 5.8 eV, and 5.5 eV in this example embodiment.

Under the above conditions, a difference in the LUMO energy level between the first host 150 and the second host 155 included in the red emission layer 140 of the organic light-emitting device 100 may be equal to or larger than 0.2.

In addition, a difference in the HOMO energy level between the first host 150 and the second host 155 included in the red emission layer 140 of the organic light-emitting device 100 may be equal to or larger than 0.1.

In the red emission layer 140, which includes the first host 150 and the second host 155 having differences in the LUMO energy level and the HOMO energy level, an area for recombination of electrons and holes may be expanded compared to a limited area for recombination of the related art organic light-emitting device including a red emission layer having only a single host. Accordingly, the recombination rate of electrons and holes are increased, such that the efficiency of the red emission layer 140 is increased. As a result, the lifetime of the organic light-emitting device can be elongated.

That is, in the red emission layer of the related art organic light-emitting device including only a single host, the area for recombination is only formed at the interface between the hole transporting layer and the red emission layer. In contrast, in the red emission layer 140 of the organic light-emitting device 100 according to the present disclosure including the first host 150 and the second host 155 having differences in the LUMO energy level and the HOMO energy level, the area for recombination of electrons and holes moves into the red emission layer 140 and can be expanded. As the recombination rate of the electrons and holes increases, the efficiency of the red emission layer 140 can thus also be increased. As a result, the lifetime of the organic light-emitting device can be elongated.

In addition, the mobility of each of the first host 150 and the second host 155 included in the red emission layer 140 of the organic light-emitting device 100 can be between $10^{-4}$ cm$^2$/Vs and $10^{-6}$ cm$^2$/Vs, so that electrons and holes are recombined well in the red emission layer 140.

Figure 3:
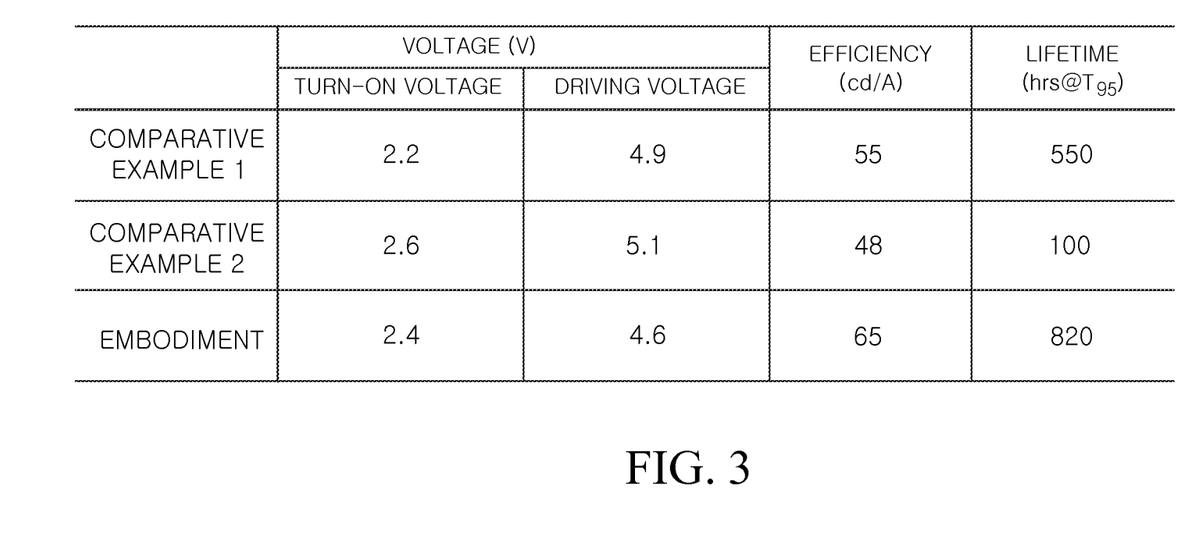
FIG. 3 is a table showing evaluation results of electro-optical characteristics of the organic light-emitting device according to an example embodiment of the present disclosure.

FIG. 3 is a table showing evaluation results of electro-optical characteristics of the organic light-emitting device according to an example embodiment of the present disclosure.

The table shown in FIG. 3 shows turn-on voltage in V, driving voltage in V, luminous efficiency in cd/A, and lifetime characteristics of red organic light-emitting devices according to Comparative Examples 1 and 2 and the example embodiment of the present disclosure.

In Comparative Example 1, the electro-optical characteristics of the related art red organic light-emitting device was evaluated which includes a red emission layer formed of a single host made of a carbazole-based material and a dopant.

In Comparative Example 2, the electro-optical characteristics of the related art red organic light-emitting device was evaluated which includes a red emission layer formed of a single host made of a metal complex and a dopant.

In an example embodiment of the present disclosure, the electro-optical characteristics of a red organic light-emitting device according to an example embodiment of the present disclosure was evaluated. Such device includes the red emission layer 140 formed by mixing the first host made of a carbazole-based material, the second host made of a metal complex and a dopant in the red emission layer.

The turn-on voltage and driving voltage characteristics of the red organic light-emitting device will be described in comparison with those of Comparative Examples 1 and 2. In Comparative Example 1, the red organic light-emitting device exhibited the turn-on voltage of 2.2 V and the driving voltage of 4.9 V. In Comparative Example 2, the red organic light-emitting device exhibited the turn-on voltage of 2.6 V and the driving voltage of 5.1 V. In contrast, in the example embodiment of the present disclosure, the red organic light-emitting device exhibited the turn-on voltage of 2.4 V and the driving voltage of 4.6 V.

As can be seen from the above results, the turn-on voltage of the red organic light-emitting device according to the example embodiment of the present disclosure was similar to that of each of Comparative Examples 1 and 2. However, the driving voltage of the red organic light-emitting device according to the example embodiment of the present disclosure was reduced by approximately 0.3 V to 0.5 V compared to each of Comparative Examples 1 and 2. Accordingly, it can be seen that the driving voltage of the red organic light-emitting device according to the present disclosure was improved.

As can be seen from the above results, the red organic light-emitting device, which includes the red emission layer 140 formed by mixing the first host made of a carbazole-based material, the second host made of a metal complex and a dopant in the red emission layer, can reduce the driving voltage and thus improve power consumption.

Then, the luminous efficiency of the red organic light-emitting device according to an example embodiment of the present disclosure will be described in comparison with those of Comparative Examples 1 and 2. In Comparative Example 1, the red organic light-emitting device exhibited the luminous efficiency of 55 cd/A. In Comparative Example 2, the red organic light-emitting device exhibited the luminous efficiency of 48 cd/A. In contrast, the organic light-emitting device according to the present disclosure exhibited the luminous efficiency of 65 cd/A.

That is, the luminous efficiency of the red organic light-emitting device according to the present disclosure is improved by approximately 10 cd/A to 17 cd/A compared to each of Comparative Examples 1 and 2.

As can be seen from the above results, the red organic light-emitting device according to an example embodiment of the present disclosure, which includes the red emission layer 140 formed by mixing the first host made of a carbazole-based material, the second host made of a metal complex and a dopant in the red emission layer, can increase efficiency and thus improve image quality.

Figure 4:
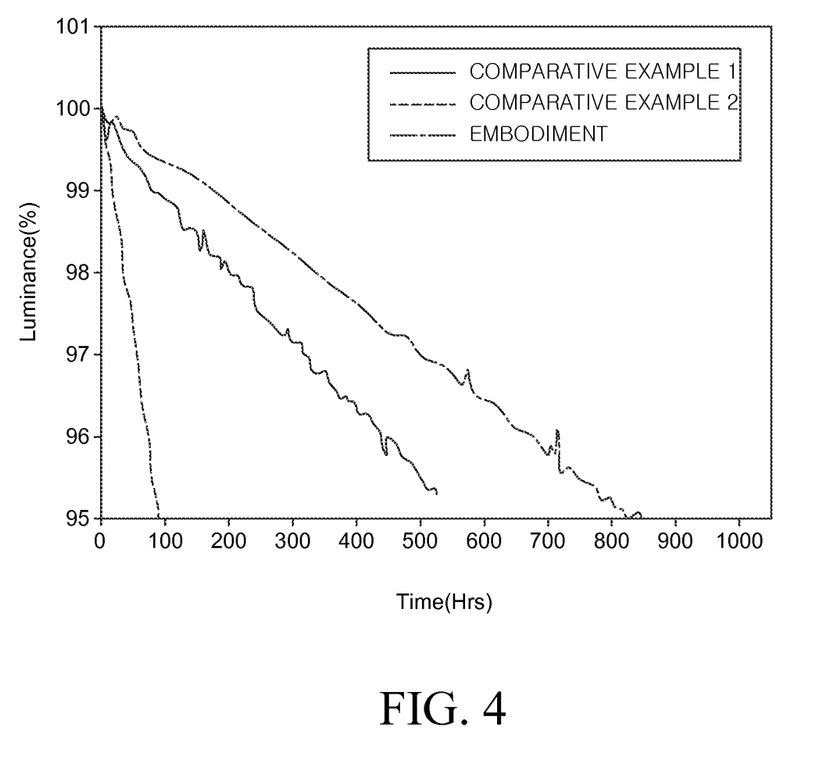
FIG. 4 is a graph showing evaluation results of lifetime of the organic light-emitting device according to an example embodiment of the present disclosure.

FIG. 4 is a graph showing evaluation results of lifetime of the organic light-emitting device according to an example embodiment of the present disclosure.

The results of lifetime characteristics of the red organic light-emitting devices according to an example embodiment of the present disclosure will be described in comparison with that of each of Comparative Examples 1 and 2 based on the results shown in FIGS. 3 and 4. In Comparative Example 1, it took approximately 550 hours until the luminance of the organic light-emitting device decreases to 95% of the initial luminance. In other words, the operating lifetime was approximately 550 hours. In Comparative Example 2, the operating lifetime was approximately 100 hours. In contrast, in the example embodiment of the present disclosure, the operating lifetime was approximately 820 hours. Accordingly, the lifetime of the organic light-emitting device according to the example embodiment of the present disclosure was improved compared to Comparative Examples 1 and 2.

As can be seen from the results, the red organic light-emitting device according to the example embodiment of the present disclosure, which includes the red emission layer 140 formed by mixing the first host made of a carbazole-based material, the second host made of a metal complex and a dopant in the red emission layer, can elongate the lifetime of the organic light-emitting device by increasing the efficiency of the red emission layer 140.

Briefly summarizing the results of the above experiments, in the organic light-emitting device according to the example embodiment of the present disclosure, the first host made of a carbazole-based material, the second host made of a metal complex and a dopant are mixed in the red emission layer. They are mixed so that driving voltage of the organic light-emitting device can be reduced, and thus power consumption of the organic light-emitting device can be improved.

In addition, by mixing the first host and the second host having differences in energy level in the red emission layer, the luminous efficiency of the red emission layer of the organic light-emitting device can be improved. Thus, the lifetime of the organic light-emitting device can be elongated.

It will be apparent to those skilled in the art that various modifications and variations can be made in the organic light-emitting device of the present invention without departing from the spirit or scope of the invention. Thus, it is intended that the present invention cover the modifications and variations of this invention provided they come within the scope of the appended claims and their equivalents.

What is claimed is:

1. An organic light-emitting device, comprising:
a first electrode and a second electrode; and
an emission layer disposed between the first electrode and the second electrode over a plurality of sub-pixel regions, the emission layer comprising a red emission layer, a green emission layer and a blue emission layer,
wherein the red emission layer comprises a first host, a second host and a dopant, wherein the first host is made of a carbazole-based material, and the second host is made of a beryllium-based complex or an aluminum-based complex.

2. The organic light-emitting device of claim 1, wherein a lowest unoccupied molecular orbital (LUMO) energy level of the first host is between 2.2 eV and 2.8 eV, and a highest occupied molecular orbital (HOMO) energy level of the first host is between 5.1 eV and 5.7 eV.

3. The organic light-emitting device of claim 1, wherein a LUMO energy level of the second host is between 2.4 eV and 3.0 eV, and a HOMO energy level of the second host is between 5.2 eV and 5.8 eV.

4. The organic light-emitting device of claim 1, wherein a difference between a LUMO energy level of the first host and a LUMO energy level of the second host is equal to or larger than 0.2 eV.

5. The organic light-emitting device of claim 1, wherein a difference between a HOMO energy level of the first host and a HOMO energy level of the second host is equal to or larger than 0.1 eV.

6. The organic light-emitting device of claim 1, wherein a mobility of each of the first host and the second host is between $10^{-4}$ cm$^2$/Vs and $10^{-6}$ cm$^2$/Vs.

7. The organic light-emitting device of claim 1, wherein a mixing ratio between the first host and the second host in the red emission layer is between 1:3 and 3:1.

8. The organic light-emitting device of claim 2, wherein the first host is made of one of CBP, CDBP and mCP.

9. The organic method device of claim 1, wherein a thickness of the red emission layer is between 300 Å and 500 Å.

10. The organic light-emitting device of claim 1, wherein the dopant is made of a phosphorescent material.

11. The organic light-emitting device of claim 1, wherein a doping concentration of the dopant is between 1% and 10%.

12. An organic layered structure, comprising:
a red emission layer comprising a first host having a lowest unoccupied molecular orbital (LUMO) energy level and a highest unoccupied molecular orbital (HOMO) energy level and a second host having a LUMO energy level and a HOMO energy level that are different from those of the first host, resulting in an area for recombination of electrons and holes being formed within the red emission layer;
a green emission layer; and
a blue emission layer,
wherein the area for recombination being expanded compared to a related art red emission layer having only a single host resulting in an area for recombination being formed only at an interface between a hole transporting layer and the red emission layer, and
the red emission layer, the green emission layer and the blue emission layer are not overlapped with each other, and
the first host is a carbazole-based material and the second host is a metal complex.

13. The structure of claim 12, wherein a mixing ratio between the first host and the second host in the red emission layer is between 1:3 and 3:1.

14. The structure of claim 13, wherein the first host is made of one of CBP, CDBP and mCP.

15. The structure of claim 14, wherein the second host is made of a beryllium-based complex or an aluminum-based complex.

16. The structure of claim 15, wherein the red emission layer, the green emission layer, and the blue emission layer are implemented in an organic light-emitting display device.

* * * * *